United States Patent
Pekar et al.

(10) Patent No.: US 10,955,536 B2
(45) Date of Patent: Mar. 23, 2021

(54) ULTRASOUND SYSTEM WITH A TISSUE TYPE ANALYZER

(71) Applicant: KONINKLIJKE PHILIPS N.V., Eindhoven (NL)

(72) Inventors: Martin Pekar, Eindhoven (NL); Wendy Uyen Dittmer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/344,401

(22) PCT Filed: Oct. 25, 2017

(86) PCT No.: PCT/EP2017/077333
§ 371 (c)(1),
(2) Date: Apr. 24, 2019

(87) PCT Pub. No.: WO2018/077962
PCT Pub. Date: May 3, 2018

(65) Prior Publication Data
US 2020/0049807 A1 Feb. 13, 2020

(30) Foreign Application Priority Data
Oct. 27, 2016 (EP) .................................. 16195916

(51) Int. Cl.
*G01S 7/52* (2006.01)
*A61B 8/00* (2006.01)
(Continued)

(52) U.S. Cl.
CPC ............ *G01S 7/5208* (2013.01); *A61B 8/585* (2013.01); *B06B 1/0292* (2013.01); *B06B 1/20* (2013.01);
(Continued)

(58) Field of Classification Search
None
See application file for complete search history.

(56) References Cited

U.S. PATENT DOCUMENTS

| 5,873,830 A | * | 2/1999 | Hossack | ............. G01S 7/52046 600/447 |
| 2010/0016719 A1 | * | 1/2010 | Freiburger | ............... A61B 8/00 600/443 |

(Continued)

FOREIGN PATENT DOCUMENTS

EP 2995259 A1 3/2016

OTHER PUBLICATIONS

International Search Report for International Application Serial No. PCT/EP2017/077333, filed Oct. 25, 2017, 14 pages.
(Continued)

*Primary Examiner* — Katherine L Fernandez

(57) ABSTRACT

An ultrasound system (100) for imaging a volumetric region comprising a region of interest (12) comprising: a probe having an array of CMUT transducers (14) adapted to transmit ultrasound beams and receive returning echo signals over the volumetric region; a beamformer (64) coupled to the array and adapted to control ultrasound beam transmission and provide ultrasound image data of the volumetric region; a transducer controller (62) coupled to the beamformer and adapted to vary driving pulse characteristics of the CMUT transducers, a region of interest identifier (72) enabling an identification of a region of interest on the basis of the ultrasound image data; a beam path analyzer (70) responsive to the ROI identification and arranged to detect an attenuating tissue type in between the probe and the ROI based on a depth variation in attenuation of the received signal; wherein the transducer controller is further adapted
(Continued)

to change, based on the attenuating tissue type detection, at least one parameter of the driving pulse characteristics.

18 Claims, 8 Drawing Sheets

(51) Int. Cl.
 *B06B 1/02* (2006.01)
 *B06B 1/20* (2006.01)
 *G01S 15/89* (2006.01)

(52) U.S. Cl.
 CPC ........ *G01S 7/5202* (2013.01); *G01S 7/52036* (2013.01); *G01S 15/8925* (2013.01); *G01S 15/8952* (2013.01)

(56) References Cited

U.S. PATENT DOCUMENTS

| | | | |
|---|---|---|---|
| 2012/0194107 A1 | 8/2012 | Kandori et al. | |
| 2014/0005521 A1* | 1/2014 | Kohler | A61B 5/064 600/411 |
| 2014/0180078 A1* | 6/2014 | Nair | A61B 8/5261 600/425 |
| 2016/0016198 A1* | 1/2016 | Emadi | B06B 1/0292 367/7 |
| 2016/0058426 A1 | 3/2016 | Hedlund et al. | |
| 2016/0143617 A1* | 5/2016 | Ebbini | A61B 8/4438 600/447 |
| 2017/0273658 A1* | 9/2017 | Wang | A61B 8/06 |

OTHER PUBLICATIONS

Olcum, et al., Deep-Collapse Operation Capacitive Micromachined Ultrasonic Transducers, IEEE Transactions on Ultrasonics, Ferroelectrics, and Frequency Control, vol. 58, No. 11, Nov. 2011, pp. 2475-2483.

Gibson, et al., "A Computerised Quality Control Testing System for B-Mode Ultrasound", Ultrasound in Medicine and Biology, vol. 27, No. 12, pp. 1697-1711.

Oralkan, O., et al., "Experimental Characterization of Collapse-Mode CMUT Operation", IEEE Transactions on Ultrasonics, Ferroelectrics, and Frequency Control, vol. 53, No. 8, Aug. 2006, pp. 1513-1523.

* cited by examiner

ULTRASOUND SYSTEM WITH A TISSUE TYPE ANALYZER

RELATED APPLICATIONS

This application is the U.S. National Phase application under 35 U.S.C. § 371 of International Application No. PCT/EP2017/077333, filed on Oct. 25, 2017, which claims the benefit of European Application Serial No. 16195916.8, filed Oct. 27, 2016. These applications are hereby incorporated by reference herein.

FIELD OF THE INVENTION

The invention relates to an ultrasound system for imaging a volumetric region comprising a region of interest comprising: an array of CMUT transducers adapted to transmit ultrasound beams and receive returning echo signals over the volumetric region; a beamformer coupled to the array and adapted to control ultrasound beam transmission and provide ultrasound image data of the volumetric region; a transducer controller coupled to the beamformer and adapted to vary driving pulse characteristics of the CMUT transducers; and a region of interest (ROI) identifier enabling an identification of a region of interest on the basis of the ultrasound image data, and which identifier is adapted to generate identification data indicating the region of interest within the volumetric region.

The present invention further relates to a method of variable frequency ultrasound imaging of a volumetric region using such an ultrasound system.

BACKGROUND OF THE INVENTION

An ultrasound imaging system with a CMUT transducer array is known from WO2015028314 A1. This probe comprises an array having CMUT cells arranged to operate in either of the following modes: a conventional mode, wherein a DC bias voltage sets a CMUT membrane of the cell to vibrate freely above a cell floor during operation of the CMUT cell; and a collapsed mode, wherein the DC bias voltage sets the CMUT membrane of the cell to be collapsed to the cell floor during operation of the CMUT cell. An increase in the DC bias voltage results in an increase in a center frequency of the frequency response of the CMUT cell during the operation the collapsed mode, and a decrease in the DC bias voltage results in a decrease in the center frequency of the frequency response of the CMUT cell during the operation in the collapsed mode. The DC bias voltage can be selected for different clinical applications depending on the frequency at which a volumetric region of the body is imaged.

There is need in new imaging techniques enabling high resolution imaging of a region of interest in the volume by further utilizing the perspectives of the CMUT technology.

SUMMARY OF THE INVENTION

It is an object of the present invention to provide an ultrasound system, which enables improved capabilities in the ultrasound imaging.

This object is achieved according to the invention by providing a beam path analyzer responsive to the identification data and coupled to the beamformer, said beam path analyzer arranged to detect an attenuating tissue type in between the CMUT array and the ROI based on a depth variation in attenuation of the received signal; wherein the transducer frequency controller is further adapted to adjust, based on the attenuating tissue type detection, at least one parameter of the driving pulse characteristics. The invention uses agility of the driving pulse characteristics of the CMUT transducers in providing a new imaging technique that allows on fly adapting optimal driving scheme applied to the CMUT array depending on the tissue type being imaged. Once the ROI is identified, the beam path analyzer analyses an attenuation of the received by the array echo signals and a change of this attenuation with depth. Different tissues show different scattering and absorption properties for the ultrasound wave propagation, which manifests in different ultrasound wave attenuation with its depth of propagation. Upon a detection of the specific tissue type, the ultrasound system of the present invention is capable of adjusting the driving pulse characteristics according to the optimal imaging conditions suitable for the detected tissue type.

The detectable attenuating tissue type can be blood and a soft tissue. Scattering properties of blood substantially differ from the properties of soft tissues. Blood shows one of the lowest attenuations (among tissue types contains in the body) of the acoustic waves. Bloods attenuation coefficient is about 0.14-0.2 dB/(MHz×cm), therefore causing a smaller reduction of the amplitude of the acoustic wave propagating along a given distance compared to the wave's propagation in any other soft tissue along the same distance. This results in a distinct difference between the attenuation slopes of the received echo signals, when they travel through the blood pool and another soft tissue. This difference in slopes can be detected by the path analyzer.

In an embodiment, the at least one parameter of the driving pulse characteristics is an ultrasound beam frequency or a bias voltage applied to the CMUT transducer.

This embodiment combines a linear scaling with frequency of the absorption coefficient with obtained by the system knowledge about the tissue types causing said absorption. This enables the system to improve a spatial resolution of the ultrasound image including the ROI by varying the frequency of the transmitted ultrasound beams. The value of applied bias voltage allows not only adjusting the operational frequency of the transducer, but also its bandwidth giving more flexibility in defining optimal imaging conditions.

In a further embodiment, when the beam path analyzer detects blood in between the array or a probe housing said array and the ROI, the transducer controller changes the ultrasound frequency from a first frequency to a second frequency being larger than the first frequency, wherein said first frequency is an optimal frequency for the soft tissue imaging.

Since blood attenuates acoustic waves less than the soft tissue an ultrasound beam with the second frequency would travel a longer distance in blood before its amplitude is reduced to the threshold value (defined by the noise level) compared to the same frequency ultrasound beam traveling through the soft tissue. Therefore, this embodiment provides an opportunity to increase a spatial resolution of the acquired ultrasound image by keeping a penetration depth at about the same value.

In yet another embodiment, the transducer controller is further adapted to change a second parameter of the driving pulse characteristics second parameter being a duty factor.

Another driving pulse characteristic, which may affect imaging properties is a duty factor, which is characterized by a number of cycles of the driving pulse. It is measured in percentage and defines a ratio of the active transmits (cycles) occurring during a pulse period. The higher the duty factor is the more cycles are used during a given driving pulse period resulting in higher acoustic energy transmitted into the tissue. Therefore, higher duty factor would result in higher penetration depth of the ultrasound beam.

In another embodiment, when the beam path analyzer detects blood in between the array or the probe and the ROI, the transducer controller changes the ultrasound frequency from a first frequency to a second frequency being higher than the first frequency; and a first duty factor to a second duty factor being higher than the first duty factor, wherein said first frequency and first duty factor are optimal driving pulse characteristics for the soft tissue imaging.

This embodiment combines an advantage of selecting an optimal image frequency for the given beam path from the array (or probe) to the ROI's location and an optimal duty factor, which provides an improved image resolution of the acquired ultrasound image. An increase in the duty factor used for the pulse with higher ultrasound frequencies improves the penetration depth of the ultrasound probe.

In yet following embodiment the transducer controller is adapted to adjust at least one parameter of the driving pulse characteristics only for the ultrasound beams transmitted within the ROI.

This embodiment provides a possibility to increase the beam frequencies in a portion of the volumetric region in which the ROI is located and thereby providing a further flexibility to a user in acquiring the ultrasound image of the volume having regions with a different penetration depth and spatial resolution.

In an embodiment, the beamformer provides the ultrasound image data having a relatively low spatial resolution within the volumetric region and relatively high spatial resolution within the region of interest.

In this embodiment increasing of the beam frequency transmitted over the region of interest allows the beamformer receiving the higher frequency echo signals originating from the ROI; thus, providing a higher resolution ultrasound data of the identified ROI. Compared to the prior art systems the ultrasound system of the present invention is capable of setting optimal ultrasound beam driving conditions for receiving more detailed ultrasound information on the volumetric region during the ultrasound scan.

In a further embodiment, the image processor produces a wide view of the volumetric region based of the low spatial resolution data and a detail view of the region of interest based on the high spatial resolution data.

Acoustic wave attenuation increases with increasing frequency. Therefore, it may be beneficial producing the wide view of the volumetric region with larger penetration depth but reduced spatial resolution and the detailed field view within the wide field of view, wherein the ROI can be imaged with higher spatial resolution. The advantage of the present invention that both fields of view can be produced using the same CMUT transducer array during a single ultrasound scan.

In another embodiment, the ultrasound system further comprises an image display coupled to the image processor, which displays both the wide view of the volumetric region and the detail view of the region of interest. Both fields of view may be displayed to a user either next to each other as separate ultrasound images or in a spatial registration as one ultrasound image.

In yet another embodiment the ultrasound system further comprises a user interface coupled to the ROI identifier and responsive to a manual selection of the ROI within the volumetric region.

This gives the user an opportunity to manually select the ROI to be identified by the ROI identifier. Optionally, the user interface can be also coupled to the frequency control, such that the user can also select the relatively low and high frequencies of the beams steered within the volumetric region and within the region of interest correspondingly.

In a further embodiment the array is a two-dimensional array or one-dimensional array.

Depending on the array's design the ultrasound system may be providing the three dimensional ultrasound images or two dimensional ultrasound images (2D slices) of the volumetric region.

DETAILED DESCRIPTION OF EMBODIMENTS

Figure 1:
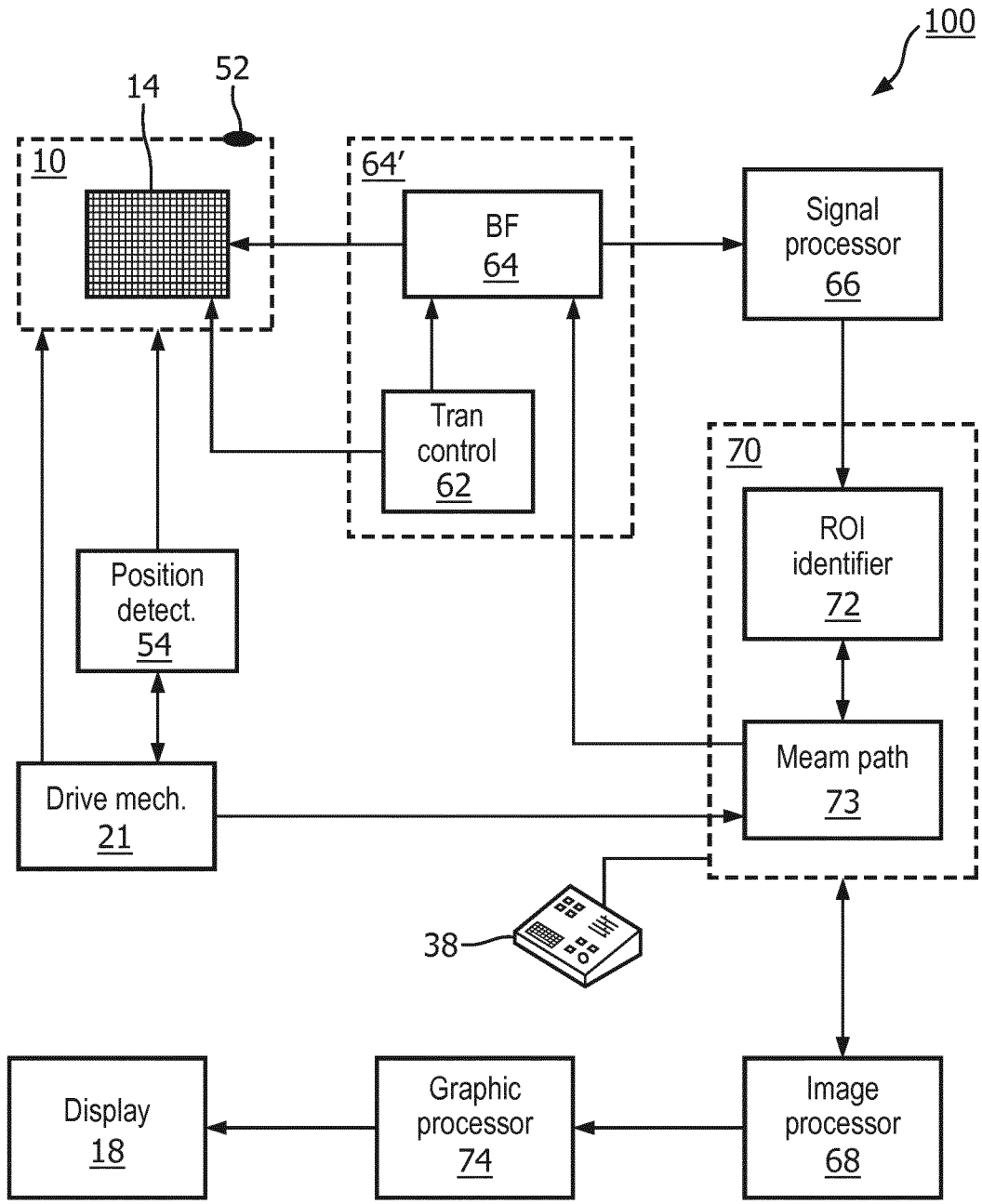
FIG. 1 illustrates an ultrasound system for imaging of a volumetric region in accordance with the principles of the present invention.

FIG. 1 shows schematically and exemplarily an ultrasound system 100 for variable frequency imaging of a volumetric region in accordance with the principles of the present invention. A probe 10 comprises an array 14 of capacitive micromachined ultrasound transducers (CMUTs) suitable for operation in a collapsed mode. This array 14 can be either two dimensional or one dimensional array. The probe can be of any ultrasound probe type: a regular ultrasound diagnostic probe, an interventional ultrasound probe or a low profile ultrasound probe (patch) suitable to be attached to a patient for a longer period of time.

The CMUTs of the array transmit ultrasound beams over a volumetric field of view 131 (FIG. 5) (comprising the volumetric region) and receive echoes in response to the transmitted beams. The transducers of the array 14 transducer are coupled to a beamformer 64, which controls a steering of the ultrasound beams transmitted by the CMUTs of the array transducer 14. The beamformer further beamforms echoes received by the transducers. Beams may be steered straight ahead from (orthogonal to) the transducer array 14, or at different angles for a larger field of view. Optionally, the ultrasound system may have a plurality of microbeamformers (not shown) each coupling groups of the individual transducers with the beamformer 64. The microbeamfomers (sub-array beamformer) partially beamforms the signals from the groups of the transducers thereby reducing amount of signal channels coupling the probe and main acquisition system. The microbeamformers are preferably fabricated in an integrated circuit form and located in the housing of the probe 10 near the array transducer. The probe 10 may further include a position sensor 52 which provides signals indicative of the position of the probe 10 to a transducer position detector 54. The sensor 52 may be a magnetic, electromagnetic, radio frequency, infrared, or other type of sensor.

The partially beamformed signals produced by the microbeamformers are forwarded to a beamformer 64 where partially beam-formed signals from individual groups of transducers are combined into a fully beam-formed signal. The ultrasound system 100 further comprises a transducer controller 62 coupled to the CMUT array 14 and the beamformer 64 (or optionally to the plurality of microbeamformers). The transducer controller 62 controls driving pulse characteristics, such as operational frequency and the duty factor, of the CMUT transducers. The fully beam-formed signal (i.e. echo signals along the beams) represent ultrasound image data, which are processed by filtering, amplitude detection, Doppler signal detection, and other processes by a signal processor 66. The ultrasound data are then processed into ultrasound image signals in the coordinate system of the array or probe (r,θ,φ for example) by an image processor 68. The ultrasound image signals may be further converted to a desired ultrasound image format (x,y,z Cartesian coordinates, for example) by a graphic processor 74 and displayed on a display 18.

A region of interest identifier 72 enables an identification of a region of interest on the basis of the ultrasound image data provided by the beamformer. The region of interest identifier 72 is adapted to generate identification data indicating a region of interest 82' (ROI) within the volumetric field of view 131. The identification data are fed to the input of a beam path analyzer 70 responsive to the identification data and coupled to the beamformer. The beam path analyzer 70 analyses echo signals received along a path between the ROI's identified location and the probe (probe's distal end). Based on a depth variation in attenuation of these received signal the analyzer is able to detect and distinguish a tissue type located in between the probe (or array) and the ROI. Since the array is affixed within the probe, the result of the detection of the tissue type in between the ROI and the array is the same as in between the ROI and the probe. Both the beam path analyzer 70 and the ROI identifier 72 can be a part of one image analyses unit 68'. The ultrasound imaging system 100 may be controlled by a user interface 38. In particular the user interface 38 can be connected to the ROI identifier 72 or directly to the image analyses unit 68' permitting a manual selection of the ROI 82' based on an ultrasound image displayed on the display 18.

In accordance to one of the embodiments of the present invention the variation of the imaging frequency of the ultrasound system is provided using CMUT transducers adapted to operate in a collapsed mode. CMUT technology allows the tuning of the imaging frequency by changing the bias voltage. This frequency range extends over a broad range and on top of this range at each frequency there is also a bandwidth which for a substantial part is close to 100%. This large frequency variability allows for imaging over a wide range of penetrations and resolutions.

The CMUT transducer array 14 of the present invention comprises a plurality of CMUT cells (transducers). Each CMUT cell 103 typically comprises a flexible membrane or diaphragm 114 suspended above a silicon substrate 112 with a gap or cavity 118 there between. A top electrode 120 is located on the diaphragm 114 and moves with the diaphragm. A bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 112 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 2 the bottom electrode 122 is grounded by way of non-limiting example. Other arrangements, e.g. a grounded top electrode 120 or both top electrode 120 and bottom electrode 122 floating are of course equally feasible.

The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 103 shall be understood as the biggest lateral dimension of the cell.

The bottom electrode 122 may be insulated on its cavity-facing surface with an additional layer (not pictured). A preferred electrically insulating layer is an oxide-nitride-oxide (ONO) dielectric layer formed above the substrate electrode 122 and below the membrane electrode 120 although it should be understood any electrically insulating material may be contemplated for this layer. The ONO-dielectric layer advantageously reduces charge accumulation on the electrodes which leads to device instability and drift and reduction in acoustic output pressure.

An example fabrication of ONO-dielectric layers on a CMUT is discussed in detail in European patent application EP 2,326,432 A2 by Klootwijk et al., filed Sep. 16, 2008 and entitled "Capacitive micromachined ultrasound transducer." Use of the ONO-dielectric layer is desirable with pre-collapsed CMUTs, which are more susceptible to charge retention than CMUTs operated with suspended membranes. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C. Exemplary techniques for producing the disclosed cavity 118 involve defining the cavity in an initial portion of the membrane layer 114 before adding a top face of the membrane layer 114. Other fabrication details may be found in U.S. Pat. No. 6,328,697 (Fraser).

Figure 2:
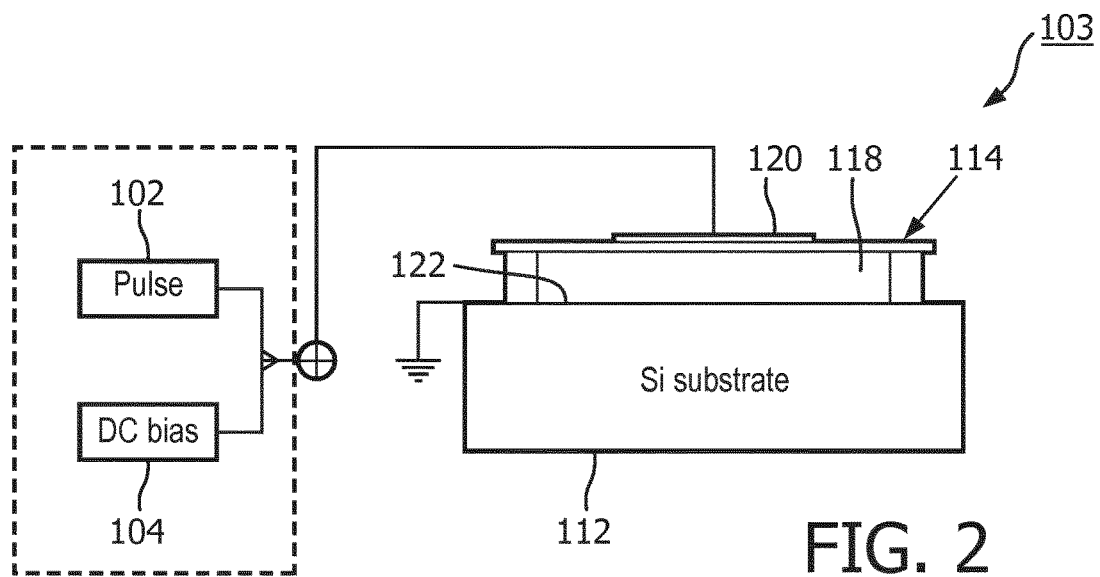
FIG. 2 illustrates a CMUT cell controlled by a DC bias voltage and driven by an r.f. drive signal.

In FIGS. 2 and 3, the diameter of the cylindrical cavity 118 is larger than the diameter of the circularly configured electrode plate 122. Electrode 120 may have the same outer diameter as the circularly configured electrode plate 122, although such conformance is not required. Thus, the membrane electrode 120 may be fixed relative to the top face of the membrane layer 114 so as to align with the electrode plate 122 below. The electrodes of the CMUT cell 100 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 100 to a received acoustic echo.

The spacing between the electrodes is controlled by applying a static voltage, e.g. a DC bias voltage, to the electrodes with a voltage supply 45. The voltage supply 45 is implemented into the transducer frequency controller 62 and provides its frequency control capabilities. The transducers of the array 14 each may have a separate voltage supply or share several voltage supplies implemented in the transducer frequency controller 62. The voltage supply 45 may also optionally comprise separate stages 102, 104 for providing the DC and AC or stimulus components respectively of the drive voltage of the CMUT cells 103. The first stage 104 may be adapted to generate the static (DC) voltage component and the second stage 102 may be adapted to generate an alternating variable voltage component or stimulus having a set alternating frequency, which signal typically is the difference between the overall drive voltage and the aforementioned static component thereof.

The second stage 102 can also enable the duty factor variation of the applied to the CMUT driving pulse. The duty factor of the driving pulse in ultrasound imaging is characterized by a number of cycles used within a period of the driving pulse. It is measured in percentage and defines a ratio of the active transmits (cycles) occurring during a pulse period. The higher the duty factor is the more cycles are used during a given driving pulse period. Increased number of the cycles improves the penetration depth in the ultrasound image by condensing acoustic energy into a narrower bandwidth of the transmit pulse. For the transmit pulse with a limited bandwidth the transducer controller sets an optimal bias voltage applied to the CMUT transducer.

The static or bias component of the applied drive voltage preferably meets or exceeds the threshold voltage for forcing the CMUT cells 103 into their collapsed states. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component. Other suitable embodiments of the voltage source supply 45 should be apparent, such as for instance an embodiment in which the voltage source supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage source supply 45 may be implemented in any suitable manner.

As is known per se, by applying a static voltage above a certain threshold, the CMUT cell 103 is forced into a collapsed state in which the membrane 114 collapses onto the substrate 112. This threshold value may depend on the exact design of the CMUT cell 103 and is defined as the DC bias voltage at which the membrane 114 sticks to (contacts) the cell floor by Van der Waals force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 3(a)-(d).

Figure 3A:
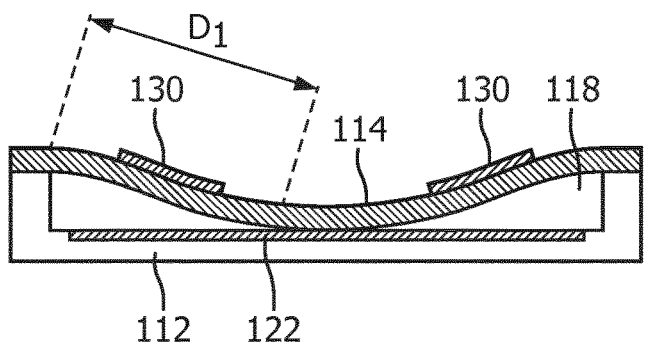
FIGS. 3a-3d illustrate the principles of collapsed mode CMUT operation applied in an implementation of the present invention.
Figure 3B:
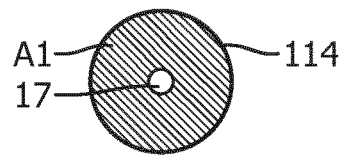
Figure 3C:
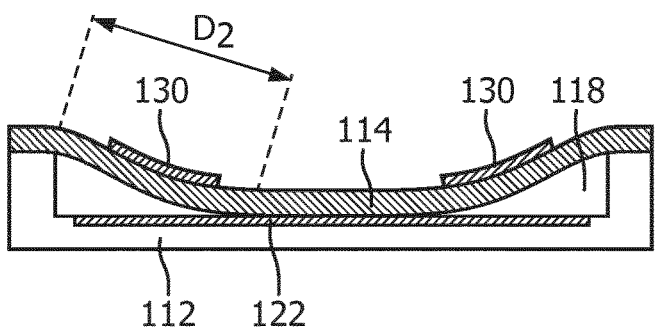

The frequency response of the collapsed mode CMUT cell 103 may be varied by adjusting the DC bias voltage applied to the CMUT electrodes after collapse. As a result, the resonant frequency of the CMUT cell increases as a higher DC bias voltage is applied to the electrodes. The principles behind this phenomenon are illustrated in FIGS. 3(a) and 3(b). The cross-sectional views of FIGS. 3(a) and 3(c) illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 3(a) when a relatively low bias voltage is applied, whereas the distance D in FIG. 3(c) is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 3(a) will be lower than the resonant frequency of the CMUT cell in FIG. 3(c) which is subject to the higher pulldown bias voltage.

Figure 3D:
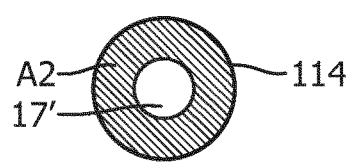

The phenomenon can also be appreciated from the two-dimensional illustrations of FIGS. 3(b) and 3(d), as it is in actuality a function of the effective operating area of the CMUT membrane. When the membrane 114 just touches the floor of the CMUT cell as shown in FIG. 3(a), the effective vibrating area A1 of the non-contacting (free vibrating) portion of the cell membrane 114 is large as shown in FIG. 3(b). The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage such as in FIG. 3(c), the greater central contact area 17' results in a lesser free vibrating area A2 as shown in FIG. 3(d). This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 4A:
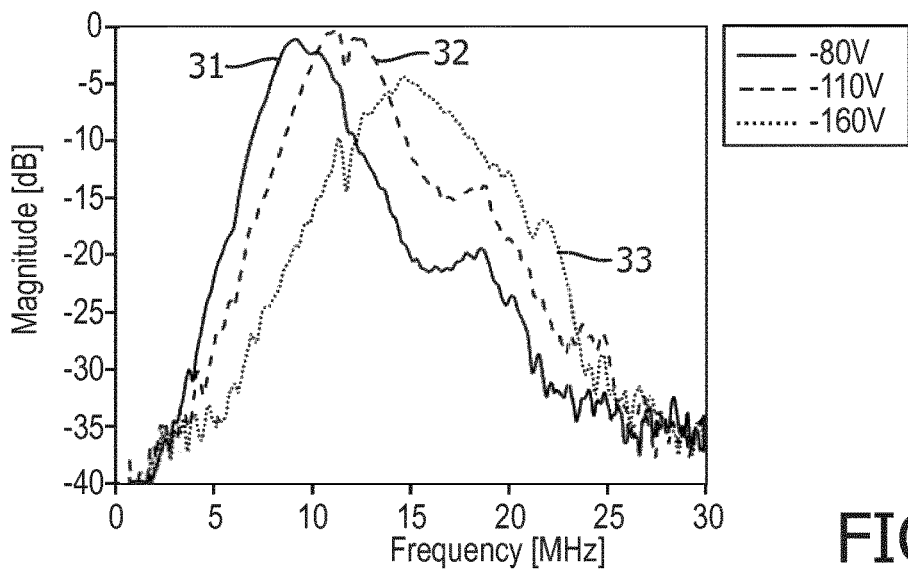
FIGS. 4a-4c show typical characteristics' of the CMUT: acoustic response as a function of frequency (A); operation frequency and bandwidth as a function of bias voltage (B); sensitivity and pulse length as a function of bias voltage (C)

For an improved imaging performance, the center frequency and the bandwidth of the transmit pulse need to match the frequency response of the CMUT, which can be tuned by the applied bias voltage. FIG. 4(a) gives an example of such a frequency tunability of the CMUT response (in dB) at three different bias voltages: −80V; −110V and −160V. At the negative bias voltage of 80V the CMUT transducer has a highest magnitude of its response around 9 MHz (curve 31); an application of −110V brings a center of the response curve 32 to about 12 MHz; and a further increase in the applied bias voltage value to −160V brings the center of the response curve 33 to about 15 MHz.

Figure 4B:
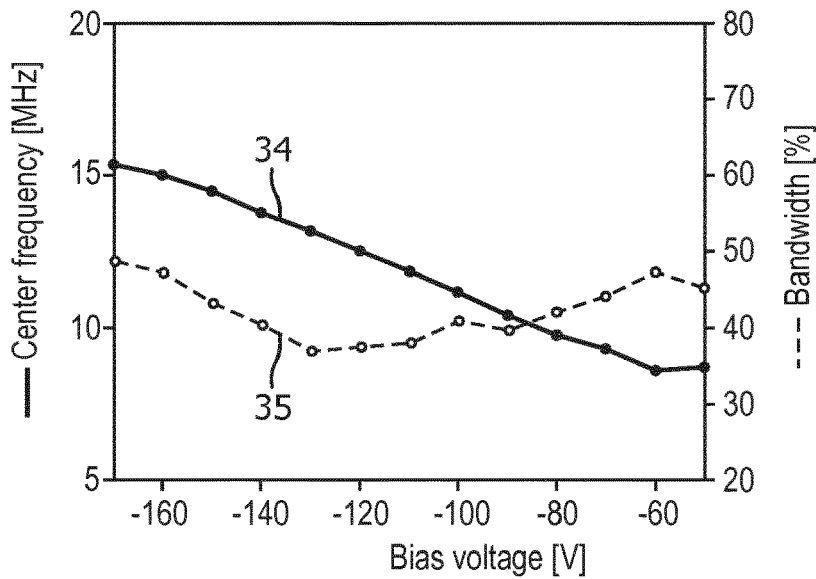
Figure 4C:
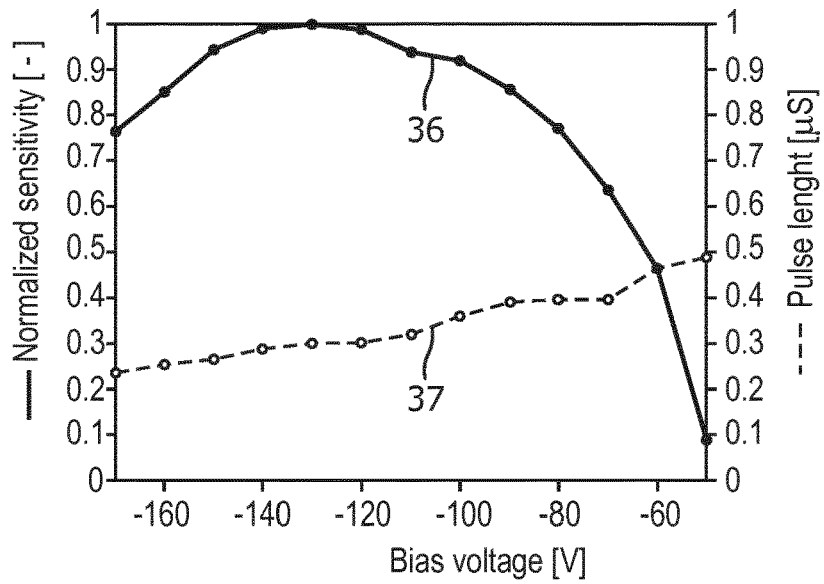

A variation of the center frequency (curve 34) and bandwidth (curve 35) of the CMUT transducer with applied bias voltage is illustrated in FIG. 4(b), these are indicative of the optimal center frequency and bandwidth of the transmit pulse (the aforementioned driving characteristics). The frequency tunability of the CMUT may come at the loss in sensitivity (curve 36) as illustrated in FIG. 4(c). Typically, loss of less than 50% is acceptable (corresponding to the bias voltage limit of about −70V in FIG. 4(c)). FIG. 4(c) further shows that decreased bias voltage (absolute value of the applied voltage) results in decreased resonance frequency and therefore longer acoustic pulse length (curve 37), which in turn translates into reduced axial resolution. Note, pulse period is proportional to the pulse length. This reduction in axial resolution is predictable based on the change in the imaging frequency (e.g. twice as low imaging frequency results in twice as low axial resolution) and can be, in an embodiment, restricted by the operator via the transducer controller, e.g. operator asks for the best driving characteristics that keep the axial resolution bellow 300 micrometers.

Figure 5A:
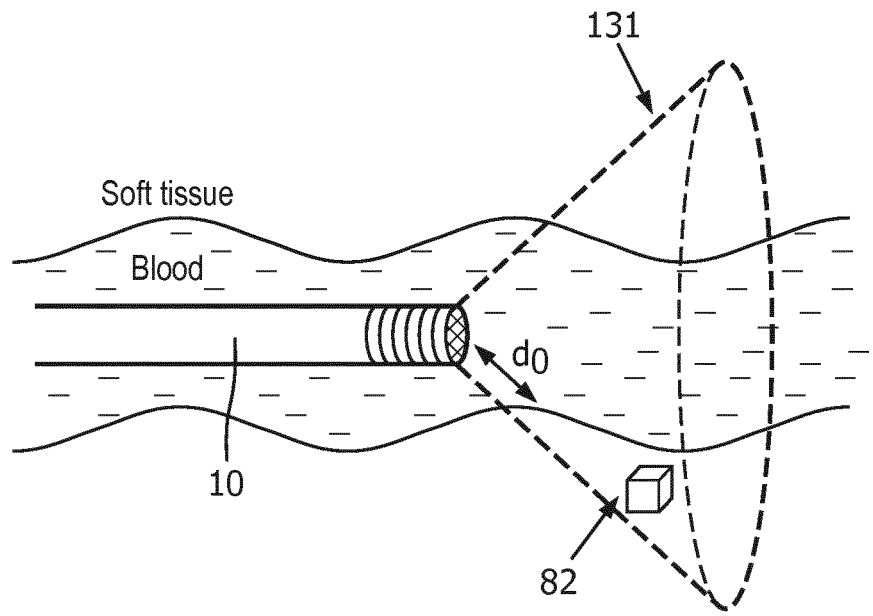
FIGS. 5a-b illustrate two possible applications of the probe suitable for intracavity imaging: for forward looking intracardiac imaging (A) and side looking imaging (B).

The present system can be used with an intracavity probe suitable for intracardiac imaging or vessel imaging. In these applications the probe (catheter) advances through the blood pool and often may perform ultrasound imaging of its surroundings. In FIG. 5(a) a forward looking ultrasound image probe located in a vessel is illustrated. The ultrasound beam steering is performed in front of the array (indicated a grid located at a tip of the probe) within the volumetric field of view 131. An identified ROI within this volumetric region is denoted as 82. Here we also illustrated an extent of the blood pool between the probe and the ROI. At an average distance $d_0$ a blood vessel wall is located. This wall separates the blood pool, wherein the probe is advancing, from the soft tissue, wherein the ROI is located. The ultrasound beams transmitted by the array towards the ROI's location would need to travel through the blood pool along $d_0$, cross the wall and enter the soft tissue. Since scattering properties of blood differ from the properties of soft tissues, the beam path analyzer 70 is arranged to analyze and identify a variation in the attenuation slopes of the received echo signals, when they travel through the blood pool and another soft tissue.

When an acoustic wave travels through a medium, its intensity diminishes with distance due to scattering and absorption. Scattering is the reflection of the sound in directions other than its original direction of propagation. Absorption is the conversion of the sound energy to other forms of energy. The combined effect of scattering and absorption is called attenuation. Ultrasonic attenuation is the decay rate of the wave as it propagates through material. The amplitude change of a decaying plane wave can be expressed as:

$$A=A_0 \exp(-\alpha x),$$

wherein $A_0$ is the unattenuated amplitude of the propagating acoustic wave at a reference location; the amplitude A is the reduced amplitude after the wave has traveled a distance x from the reference location; and α is an attenuation coefficient expressed in dB/(MHz×cm) Attenuation coefficient is generally proportional to the wave's frequency. Attenuation is generally proportional to the square of sound frequency. Quoted values of attenuation are often given for a single frequency. For example, typical tissue examples and their attenuation coefficients at a frequency of 1MHz are given in the table below:

| Tissue | Attenuation coefficient (dB/(MHz × cm) |
|---|---|
| Blood | 0.2 (20° C.) |
| Brain | 0.6 |
| Breast | 0.75 |
| Cardiac | 0.52 |
| Liver | 0.5 |
| Muscle | 1.09 |

As can be seen from the table, blood shows one of the lowest attenuations.

Therefore, the amplitude on the acoustic wave traveling the distance $d_0$ (in FIGS. 5a-b) through the blood pool will be less attenuated compared to its attenuation after traveling the same distance but through the soft tissue.

Figure 5B:
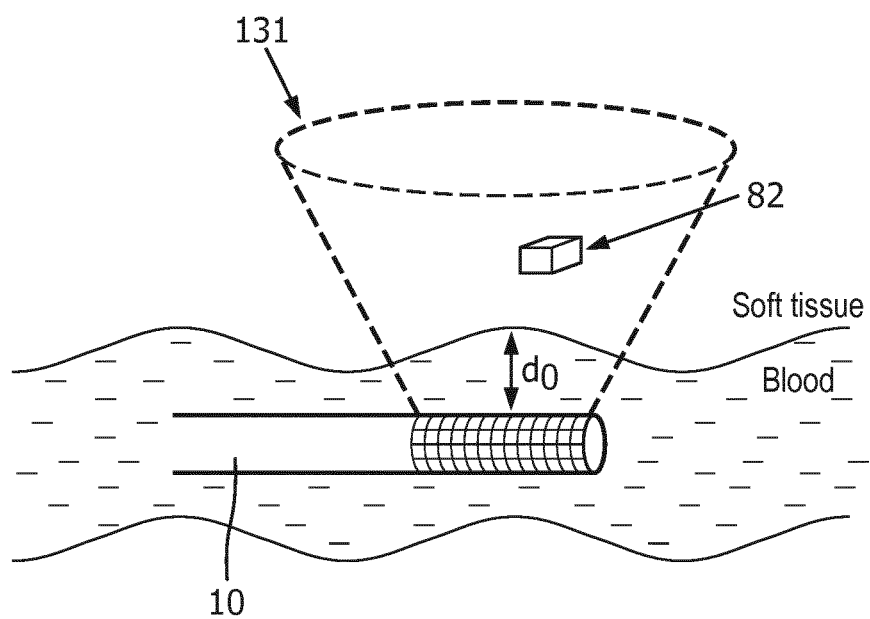

In FIG. 5(b) a side looking ultrasound image probe 10 (such as IVUS) located in a vessel is illustrated. This probe has an ultrasound array capable of ultrasound beam steering in the direction perpendicular to a main axis of the probe. When the probe advances through the blood pool in the vessel the volumetric field of view 131 located at the side of the probe is being imaged. Similarly as in a previous example the ROI 82 within the volumetric region (or a 2D slice of the volumetric region) is shown as well as the average distance $d_0$ to the blood vessel wall.

The function of the beam path analyzer of the present invention may be realized in the following way.

Figure 6A:
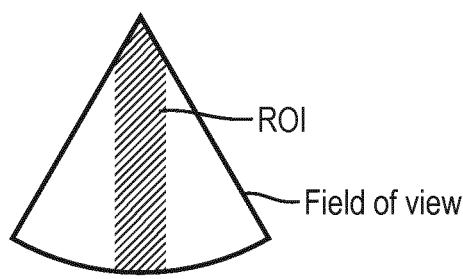
FIGS. 6a-c show: echo signal reception used for estimations of the attenuation depth variation (A); signal amplitude decrease with depth (attenuation) at a given frequency and for a given tissue segment (B); comparison of the attenuation depth variation for two ultrasound beam having different frequency and traveling through the same region (C).

The user (clinician) inputs via the user interface 38 a location of the ROI within the volumetric region. Based on this input the ROI identifier 72 generates identification data, which are further transmitted to the beam path analyzer 73. The beam path analyzer can calculate a mean signal value within the ROI along the penetration depth to obtain signal as illustrated FIG. 6(a). Further, the beam path analyzer may communicate to the beamformer to switch off the transmit pulse and to receive noise signals originating from the system. The latter reception represents a "noise image" or amount of noise present in the system. The beam path analyzer 73 is further arranged to calculate a mean noise value along the penetration depth within the same ROI. Alternatively the mean signal and noise estimations can be done using the approach described in Gibson et al., A computerized quality control testing system for B-mode ultrasound. Ultrasound in Medicine & Biology, 27(12), 1697-1711 (2001).

Figure 6B:
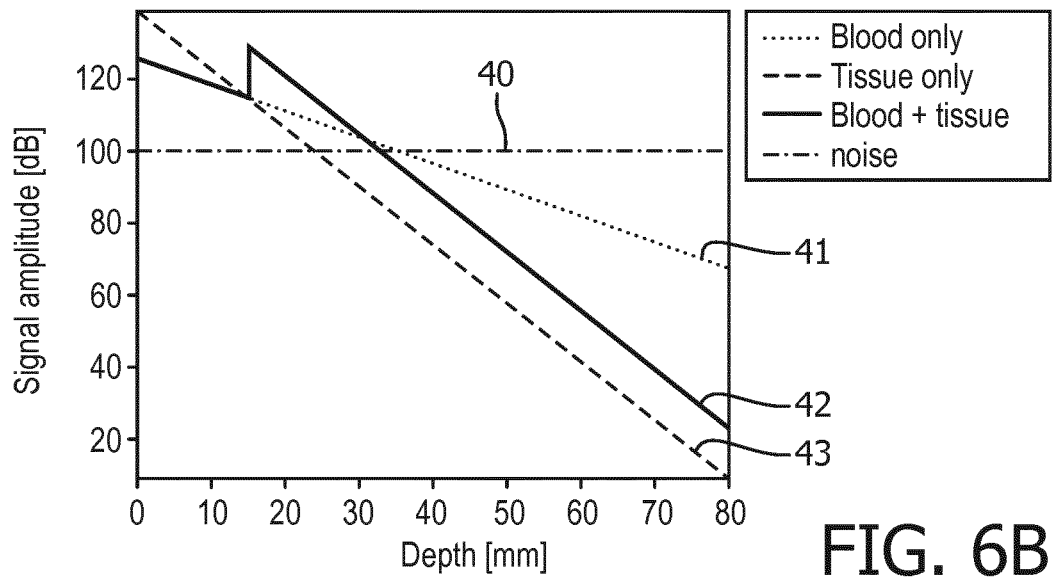

Both mean signal and noise depth variations can be compensated for a time-gain control and plotted in a dB scale as a function of depth as illustrated in FIG. 6(b). The received data signal corresponding to the acoustic wave at a given frequency and passing through the blood pool and the soft tissues 42 would have two distinct slopes of the monotonically decreasing segments, wherein each slope would be defined by the attenuation within the tissue segment the wave is traveling through. Since blood and tissue have a different acoustic impedance one can observe tissue's boundary in an ultrasound image. The tissue also has a higher back-scattering coefficient than blood, therefore the received data signal in curves 42 and 43 has a few dB increase at the tissue's boundary. An intersection between the signal 42 and noise 40 curve determines a penetration depth (or maximum distance from the probe, at which an ultrasound image can be obtained) achievable by the ultrasound system. In the example of FIG. 6(b) the penetration depth for the transmitted signal will be a sum of the distance of 15 mm, which signal travels through the blood pool, and the distance of 17.4 mm, which signals travels through the soft tissue till its amplitudes is reduced to the undistinguishable noise level. The beam path analyzer 73 enables an optimization of the drive pulse characteristics based on different attenuation properties of different tissues. As can be seen FIG. 6(b) the blood pool region attenuates the signal less than the soft tissue region, which is manifested by a smaller slope of the signal decrease in a "blood" segment compared to a larger slope of the signal decrease in a "tissue" segment (sharper reduction in the signals amplitude with the same distance).

Figure 6C:
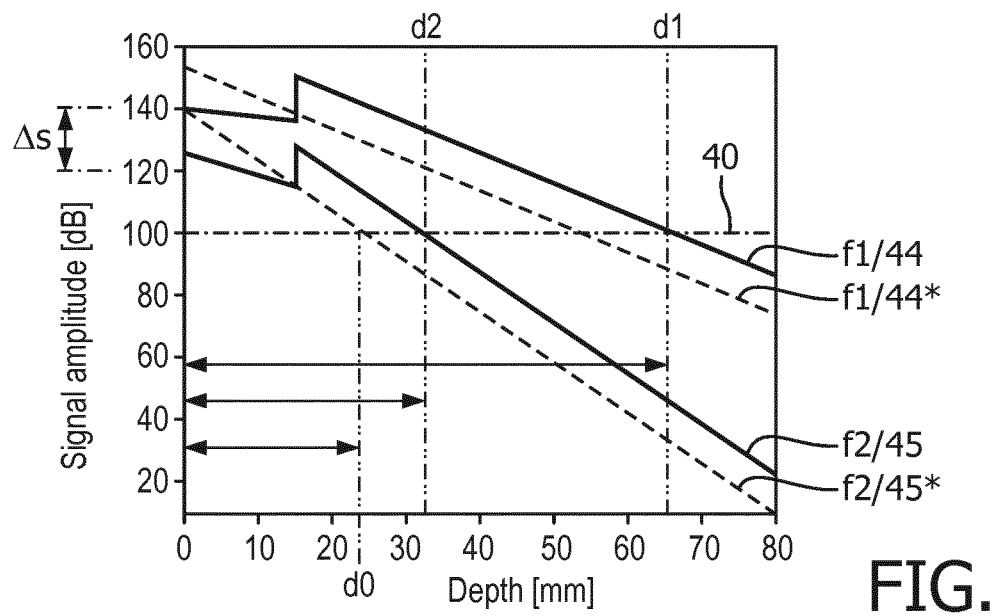

As soft tissue attenuation is proportional to the acoustic wave frequency the penetration depth of the ultrasound system can be altered by varying the transmitted beams frequency. FIG. 6c illustrates this frequency variation and gain in the penetration depth with said variation. Curve 44 corresponds to the depth attenuation of the ultrasound beam having a frequency f1. This beam passes through the blood pool located in between the probe and the ROI, said blood pool having an extent of about 15 mm. The signal curve intersects the noise curve 40 at the distance d1 from the probe. If there was no blood pool in between the ROI and probe, the amplitude of the ultrasound beam would be attenuated higher in accordance with a single soft tissue attenuation coefficient. Curve 44* shows the signal's attenuation in the absence of the blood. Curve 44* intersects the noise curve 40 at more shallow depth d2.

Let us assume that the indicated by the user location of the ROI within the volumetric region is positioned at the distance d2. Prior art systems would calculate the transmitted beam frequency based on the single soft tissue attenuation coefficient. This would result in selecting the beam frequency f1. Therefore, providing the ultrasound image data of the volume with a first spatial resolution defined by f1.

The present invention via providing a beam path analyzer 73 allows the ultrasound system to recognize the presence of the blood pool in between the probe and the ROI's location. This information is used to the user's benefit for calculating an optimal image frequency, which enables the same penetration depth d2 together with higher image resolution. Curve 45 corresponds to the depth attenuation of the ultrasound beam having a larger than f1 frequency f2. Since the beam path analyzer takes into account the reduced attenuation of the blood pool, the penetration depth for the beam signal with f2 remains the same d2. However, the increased transmission frequency f2 would result in the larger resolution ultrasound image acquired by the ultrasound system 100. For comparison, curve 45* shows the signal's attenuation for f2 in the absence of the blood. Curve 45* intersects the noise curve 40 at even shallower depth d0.

Therefore, the beam path analyzer 73 of the present invention based on the measured attenuation of the tissue within the field of view allows to optimize the driving pulse characteristics of the CMUT array in order to achieve an improved quality of acquired ultrasound images. The attenuation depth variation analyzed by the beam path analyzer 73 may also include variable sensitivity of the CMUT at different imaging frequencies (FIG. 4c). This amplitude compensation is illustrated in FIG. 6(c) by Δs.

The number of cycles affects the bandwidth and pulse length proportionally, e.g. pulse of two cycles will have half of the bandwidth and half of the pulse length as compared to the pulse of a single cycle. In general, the center frequency is not affected by the pulse length. The transmit sensitivity increases with the increased number of pulses which translates into a larger penetration depth. The higher the duty factor the more energy is transmitted into the tissue, therefore the penetration depth is better, which further allows improving the depth of ultrasound assisted visualization at the given frequency. The present invention allows optimizing the driving characteristics: pulse frequency, duty cycle and bias voltage, specific to the CMUT transducer in order to provide an optimal ultrasound image of the given region of interest depending on its anatomical environment. The trade-off for the increased penetration depth due to the increased duty factor is a potential reduction in axial resolution: twice as long pulse gives two times lower axial resolution, while lateral resolution remains about the same. Therefore, it may be further beneficial for the user to be able to select a set of two values for the spatial resolution: axial and lateral.

Once the optimal drive pulse characteristics are calculated the transducer controller 62 varies the bias and a.c. voltages applied to the CMUT array 14 accordingly. This can be understood in back reference to FIGS. 3(a) and 3(d), which explained that the resonance frequency of the CMUT cell 103 in a collapsed state is a function of the applied (DC) bias voltage. By adjusting the applied bias voltage when generating ultrasonic pulses of a particular set frequency via applying a stimulus having the appropriate set frequency, pulses of different frequencies can be generated exhibiting (near-)optimal acoustic performance of the CMUT cell 103 for each pulse frequency. This therefore ensures (near-) optimal imaging resolution over a large bandwidth of the imaging spectrum. Acoustic wave attenuation increases with increasing frequency, while ultrasound image resolution improves with increasing frequency. To meet optimal and penetration requirements reasonably, the frequency range for most diagnostic applications is 2 to 15 MHz. The lower portion of the range is useful when increased depth (e.g., the region of interest is located deeper in body) or high attenuation (e.g., in transcranial studies) is encountered. The higher portion of the frequency range is useful when little penetration is required (e.g. in imaging breast, thyroid, or superficial vessel or in pediatric imaging). In most large patients, 3-5 MHz is a satisfactory frequency, whereas in thin patients and in children, 5 and 7.5 MHz often can be used. A higher frequency range above 15 MHz can provide high resolution imaging using intracavity (intravascular) probes, such as IVUS, ICE, FL-ICE. These probes can be positioned closer to the ROI inside body cavities, vessel, etc.

Another application of the present invention can be point-of-care, wherein portable (ultramobile) ultrasound systems are used for to detect any internal bleeding (blood pool in the stomach area, for example). In this case the driving pulse characteristics of the array can be adjusted, based on the presence and extent of the blood pool, such that optimal penetration depth and resolution can be achieved in order to assess any trauma of internal organs.

Figure 7A:
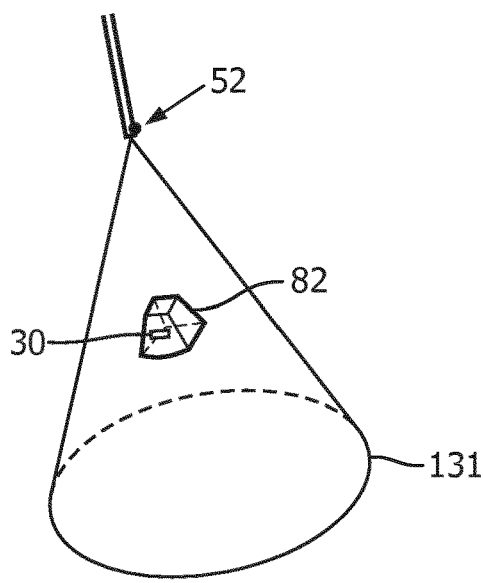
FIGS. 7a-b illustrate the scanning of the volumetric region with variable driving pulse characteristics using an ultrasound probe adapted to be moved with respect to the volumetric region.
Figure 7B:
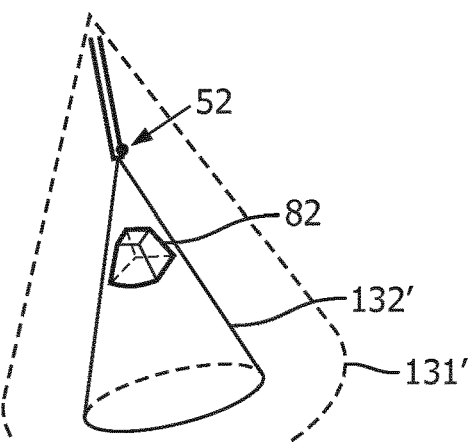

FIG. 7 illustrates an embodiment of the present invention, wherein the probe's position can be varied within a volumetric field of view 131'. The probe, for example, can be placed in a forward looking or end firing configuration such that the probe can be easily translatable towards and away from the ROI. This can be realized by providing the intracavity probe such as IVUS (intravascular ultrasound), ICE (intracardiac echocardiography), FL-ICE (forward looking intracardiac echocardiography), for example as described in EP1742580B.

The probe may include the transducer array in the distal tip which is swept to scan a volumetric region. The volume sweeping can be done either providing a mechanical movement of the 1D array or an electronic steering of the beams with the 2D array. The transducer array is contained within a fluid chamber located at the distal tip of the probe, wherein fluid provides an appropriate acoustic coupling between the probe and the imaged volumetric region. As illustrated in FIG. 1 the ultrasound system 100 may further comprise a drive mechanism 21 coupled to the probe and the ROI identifier 72 (optionally to the analyses unit 68'), wherein the drive mechanism based on the identification data acts to move the probe 10 during imaging. The drive mechanism 21 also receives the signals from the position sensor 52, which tracks the probe's spatial location, thus providing the probe's movement within the volumetric field of view 131'. This embodiment gives a higher flexibility to the upper limit of the high frequencies with which the ROI 82' can be imaged. Once the ROI is identified the image processor 68 computes coordinates of the ROI 82 and a volumetric region 132 surrounding the identified ROI in the volumetric field of view 131 based on the based on the identification data. If the distance between the transducer array 14 (or practically the probe 10) and the ROI is beyond the penetration depth of the beams with the selected high frequency, the drive mechanism 21 would be communicated to move closer towards the ROI within the volumetric field of view 131' (FIG. 7b), such that a "zoom-in" image of the ROI can be acquired.

This invention combines benefits of miniaturized CMUT transducers (enabled by advances in CMOS manufacturing) and variation in their operation band (enabled by the collapsed mode of operation) with a feedback loop to the driving device providing the user with a new generation of ultrasound system capable of automatically zooming-in and out function within the volumetric region. A combination of the wide frequency band of the CMUT array operating in the collapsed mode with means to physically translate the probe comprising this array enables a new user experience in advanced ultrasound imaging with increased details and therefore improved diagnostic imaging.

Figure 8A:
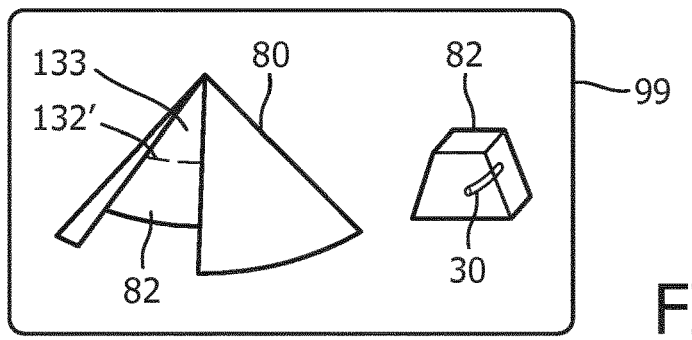
FIGS. 8a-c illustrate displays of ultrasound images of a volumetric region together with the wide view of the volumetric region comprising the detail view of the region of interest.
Figure 8B:
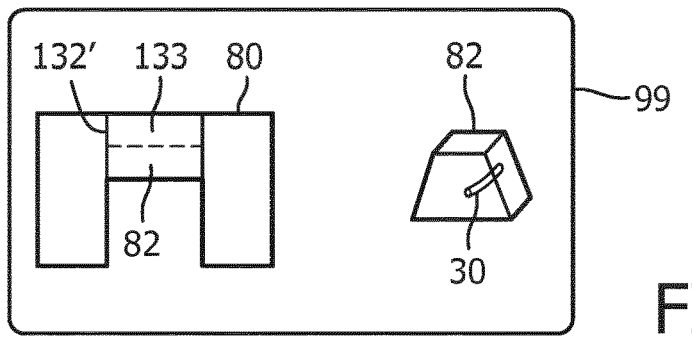
Figure 8C:
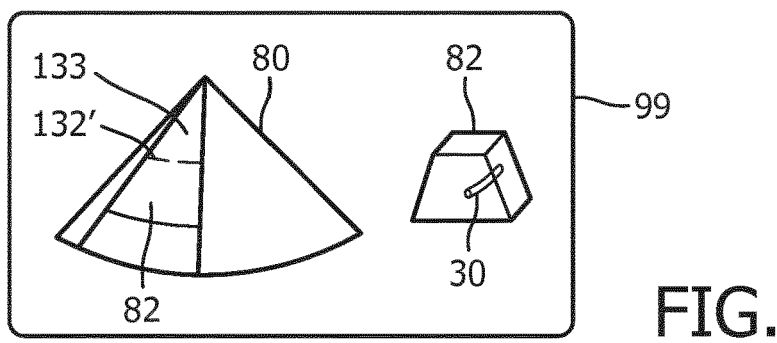

FIG. 8 illustrates a display 99 of 2D ultrasound images displayed to the user with a wide view 80 and a detail view 132' in a spatial registration with respect to each other. This figure illustrated an embodiment, wherein the ultrasound system uses two different frequencies to image the volumetric region: a higher frequency only for the region of interest and a lower frequency for the rest of the volumetric region. A representation 82 of the selected ROI 82' is displayed at the increased imaging frequency in the detail view 132'. Since the penetration depth of the ultrasound beams with relatively high frequency is reduced compared to the penetration depth of the ultrasound beams with the relatively low frequency, an upper frequency limit of the relatively high frequency range will be limited by a depth (distance to the probe) at which the ROI is located and will be taken into account by the image processor 68 during its computation. The system 100 may first acquire ultrasound data of the volumetric field of view with the relatively low beam frequencies, thus providing surrounding context of the volumetric region, and further "zoom-in" to the ROI 82 upon its identification. The detail view 132' of the ROI 82 can be updated in the real time next to the wide view 80 acquired previously and displayed for the context as illustrated in FIG. 8c.

Alternatively, the detail view 132' of the ROI 82 and the wide view 80 can be displayed next to each other. In cardiology application during heart imaging the display and acquisition of the ultrasound images may be synchronized with heart cycle by an ECG gating.

In case the CMUT array 14 is a linear arrays the transducer frequency controller 62 can address (drive) the individual transducer cells 103 with different frequencies so that the ROI is imaged at high frequency and that the other elements are maintained at low frequencies. A representative image acquired with the linear array is shown in FIG. 8b.

An embedded real time high frequency detail view 132' image is generated simultaneously to a real time low frequency wide view 80 image. This has the advantage that the surrounding context is still imaged (albeit at lower solution) in real time with relatively higher depth to allow for example orientation and navigation of tools that occur in the periphery of the ROI. It is also possible to obtain similar images if the CMUT array 14 is a phased array as shown in FIG. 8(a) and FIG. 8(c). In the phased array case the beamforming is performed such that for each line that constitutes the image, an appropriate frequency for all the transducers is chosen such that a high frequency detail view 132' image is imbedded in the wide view 80 image containing lower frequency lines. If both views: the detail view 132' of the ROI 82 and the wide view 80 are updated in real time, the system comprising the phased array can continually acquire first all lines of the volumetric field of view 131 volume at low frequency and then all lines the volumetric region 132 surrounding the identified ROI 82 with higher frequency. The acquired view can by further interleaved or interpolated into one ultrasound image. This is illustrated in FIG. 8(c). In alternative acquisition workflow the wide view 80 is updated beyond detail view 132', wherein the resulting image displayed to the user is illustrated in FIG. 8a. The former has the advantage of real time views of the whole volume, e.g. to track interventional devices. The latter has the advantage that less lines are acquired and a higher frame rate can be achieved.

Figure 9:
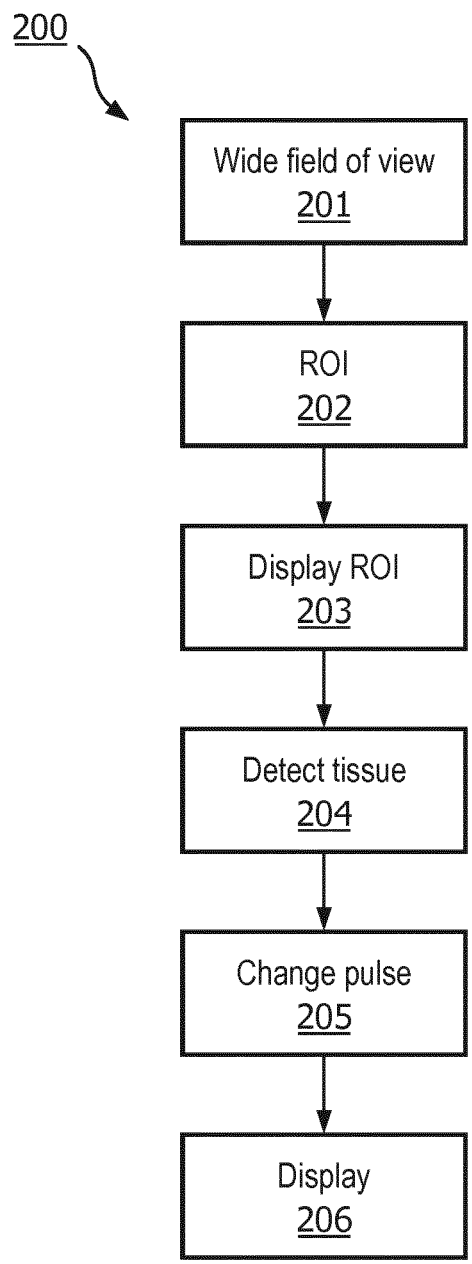
FIG. 9 illustrates a workflow of a basic principle of different drive pulse characteristics image acquisition of the present invention.

FIG. 9 illustrates a workflow 200 of image acquisition according to the present invention. At step 201 the volumetric field of view 131 is imaged with the ultrasound beam having optimal driving pulse characteristics corresponding to the soft tissue imaging. In step 202 the ROI 82 is detected by the identifier, for example, or based on the user input. In an alternative step 203 outlines of the ROI may be displayed to the user. At this stage the user can also manually interact via the user interface 38 with the systems 100 adjusting the size and/or location of the ROI. The user can also select values for the desired spatial resolution (axial and lateral resolutions). Further, in step 204 the beam path analyzer 73, based on the identification data, analyses a depth variation in attenuation of the received signals and further detects an attenuating tissue type. In step 205 the transducer controller 100 based on the attenuating tissue type detection would change at least one parameter of the driving pulse characteristics such that the detail view of the ROI with increased resolution can be acquired.

For example, for the given frequency set by the controller based on the attenuating tissue type detection the ratio of the selected axial and lateral resolutions can be also taken into account by the controller. In this case a further adjustment of the duty factor would provide the ultrasound data with selected axial and lateral resolutions. In step 206 the wide and detailed fields of view based on the acquired ultrasound data are displayed to the user.

Figure 10:
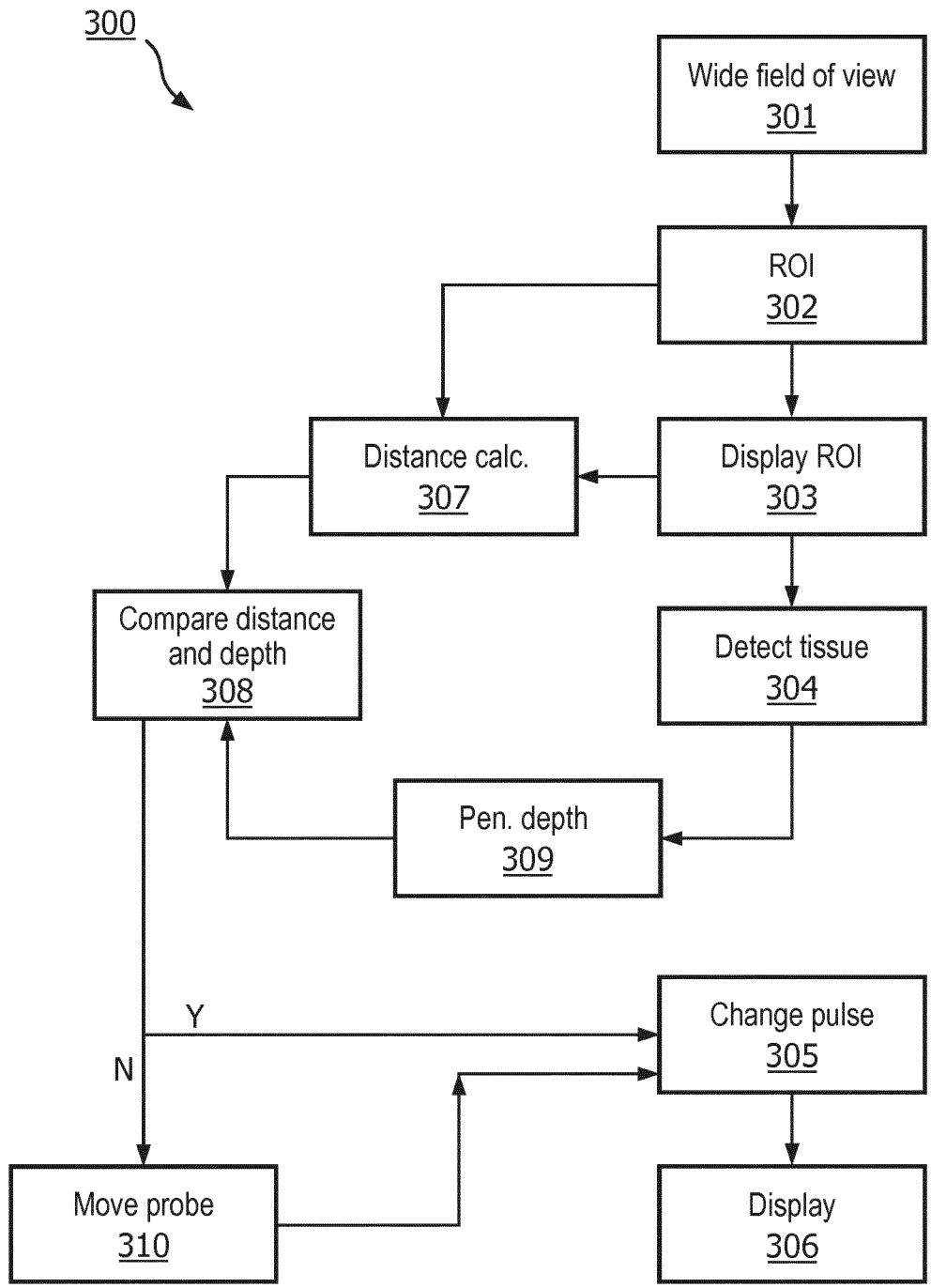
FIG. 10 illustrates a workflow for different drive pulse characteristics image acquisition in accordance with another embodiment of the present invention.

In FIG. 10 illustrates a workflow 300 for image acquisition according to another embodiment of the present invention. At step 301 the volumetric field of view 131 is acquired. In step 302 the ROI 82 is detected by the identifier. In step 303 outlines of the ROI may be displayed to the user. At this stage the user selects the desired resolution (or frequency) of the detail view of the ROI and can also manually interact via the user interface 38 with the systems 100 adjusting the size and/or location of the ROI. In parallel, in step 307 the image processor 68 computes the distance from the probe to the most distant edge of RIO. Further, in step 304 the beam path analyzer 73, based on the identification data, analyses a depth variation in attenuation of the received signals and further detects an attenuating tissue type. In step 309 based on this information the image processor 68 computes the penetration depth corresponding to the selected resolution (frequency). In step 308 the distance between the probe and the ROI is compared to the penetration depth, wherein the detected tissue type is taken into account. If the computed penetration depth is larger than the distance to the ROI, then the workflow is followed by step 305, in which the system 100 acquires the detail view of the ROI with the selected resolution and the optimized drive pulse characteristics for the selected frequency. If the computed penetration depth is smaller than the distance to the ROI, then the workflow is followed by step 310, in which the drive mechanism provides probe's movement towards the ROI's location. A movement distance is determined by the ROI location, detected attenuation tissue type and the selected (object), such that the probe cannot be moved further, the system 100' may provide a feedback to the user with a computed optimal resolution at which the ROI can be acquired taking into account anatomy limitations. Further, system 100 acquires the detail view of the ROI with the selected resolution or optimal suggested resolution in step 305. In step 306 the wide and detailed fields of view are displayed to the user.

It shall be understood by the person skilled in the art that the principles of the present invention can be practiced in both 2D and 3D ultrasound imaging.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A method of ultrasound imaging, comprising:
   transmitting ultrasound beams with a first frequency into a volume of a patient with a region of interest (ROI) using an array of capacitive micromachined ultrasound transducers (CMUTs) of an ultrasound imaging system;
   receiving, with the array, first echo signals corresponding to the ultrasound beams with the first frequency;
   providing, with a beamformer coupled to the array, first ultrasound image data based on the first echo signals, wherein the first ultrasound image data comprises a first spatial resolution of the ROI;
   identifying, with one or more processors coupled to the beamformer, a location of the ROI within the volume based on the first ultrasound imaging data;
   detecting, with the one or more processors, an attenuating tissue type between the array and the ROI based on a depth variation in attenuation of the first echo signals, using the identified location of the ROI, a signal value of the first echo signals within the ROI, and a noise level of the ultrasound imaging system, wherein the attenuating tissue type comprises blood;
   transmitting, with the array, ultrasound beams with a second frequency higher than the first frequency into the volume, in response to detecting the attenuating tissue type, wherein the second frequency is selected such that an amplitude of the ultrasound beams with the second frequency exceeds the noise level when traveling through the attenuating tissue type to the ROI;
   receiving, with the array, second echo signals corresponding to the ultrasound beams with the second frequency;
   providing, with the beamformer, second ultrasound image data based on the second echo signals, wherein the second ultrasound image data comprises a second spatial resolution of the ROI that is higher than the first spatial resolution; and
   outputting, with the one or more processors, an ultrasound image based on the second ultrasound image data.

2. The method according to claim 1, further comprising calculating an extent of a blood pool being in contact with a probe housing the array, wherein said blood pool comprises the blood.

3. An ultrasound system, comprising:
   an array of capacitive micromachined ultrasound transducers (CMUTs) adapted to:
     transmit ultrasound beams with a first frequency and a second frequency higher than the first frequency into a volume of a patient with a region of interest (ROI); and
     receive first echo signals corresponding to the ultrasound beams with the first frequency and second echo signals corresponding to the ultrasound beams with the second frequency;
   a beamformer coupled to the array and adapted to provide first ultrasound image data based on the first echo signals, wherein the first ultrasound image data comprises a first spatial resolution of the ROI;
   one or more processors coupled to the beamformer and adapted to:
   identify a location of the ROI within the volume based on the first ultrasound imaging data; and
   detect an attenuating tissue type between the array and the ROI based on a depth variation in attenuation of the first echo signals, using the identified location of the ROI, a signal value of the first echo signals within the ROI, and a noise level of the ultrasound system, wherein the attenuating tissue type comprises blood; and
   a transducer controller coupled to the beamformer and adapted to control the array to transmit the ultrasound beams with the higher second frequency into the volume, in response to the one or more processors detecting the attenuating tissue type, wherein the second frequency is selected such that an amplitude of the ultrasound beams with the second frequency exceeds the noise level when traveling through the attenuating tissue type to the ROI,
   wherein the beamformer is further adapted to provide second ultrasound image data based on the second echo signals, wherein the second ultrasound image data comprises [[higher]] a second spatial resolution of the ROI that is higher than the first spatial resolution, and
   wherein the one or more processors are further adapted to output an ultrasound image based on the second ultrasound image data.

4. The ultrasound system according to claim 3 further comprising a probe having the array of CMUTs.

5. The ultrasound system according to claim 4, wherein the one or more processors are further arranged to calculate an extent of a blood pool being in contact with the probe, said blood pool comprising the blood.

6. The ultrasound system according to claim 5, wherein the second frequency has a value defined by the extent of the blood pool.

7. The ultrasound system according to claim 4, wherein the probe is a catheter.

8. The ultrasound system according to claim 3, wherein the blood exhibits a first attenuation coefficient and the ROI comprises a soft tissue exhibiting a second attenuation coefficient, wherein the second attenuation coefficient is larger than the first attenuation coefficient.

9. The ultrasound system according to claim 3, wherein the transducer controller controlling the array to transmit the ultrasound beams with the higher second frequency comprises changing a D.C. bias voltage applied to the CMUTs.

10. The ultrasound system according to claim 3, wherein said first frequency is an optimal frequency for soft tissue imaging.

11. The ultrasound system according to claim 3, wherein the transducer controller is further adapted to adjust a duty factor associated with the array.

12. The ultrasound system according to claim 11, wherein, when the one or more processors detect the blood in between the array and the ROI, the transducer controller is further arranged to change a first duty factor to a second duty factor being higher than the first duty factor, wherein said first duty factor is an optimal driving pulse characteristic for soft tissue imaging.

13. The ultrasound system according to claim 3, wherein the transducer controller is adapted to adjust at least one parameter of driving pulse characteristics of the array only for the ultrasound beams transmitted within the ROI.

14. The ultrasound system according to claim 3, wherein the beamformer is arranged to provide the ultrasound image data having the relatively low first spatial resolution within the volume and the relatively high second spatial resolution within the region of interest.

15. The ultrasound system according to claim 14 wherein the one or more processors are responsive to the ultrasound image data, based on which the one or more processors are adapted to produce the ultrasound image, wherein the one or more processors are arranged to produce a wide view of the volume based of the low first spatial resolution data and a detail view of the region of interest based on the high second spatial resolution data.

16. The ultrasound system according to claim 15 further comprising an image display coupled to the one or more processors, wherein the image display is arranged to display both the wide view of the volume and the detail view of the region of interest.

17. The ultrasound system according to claim 16 further comprising a user interface coupled to the one or more processors and responsive to a manual selection of the ROI within the volume.

18. The ultrasound system according to claim 3, wherein the transducer controller is further configured to change at least one of a duty factor associated with the array or a D.C. bias voltage applied to the CMUTs.

* * * * *